United States Patent [19]

Dong et al.

[11] Patent Number: 4,611,076

[45] Date of Patent: Sep. 9, 1986

[54] CHIRAL CYANOHYDRINATION PROCESS

[75] Inventors: Walter Dong; Peter S. Friend, both of Houston, Tex.

[73] Assignee: Shell Oil Company, Houston, Tex.

[21] Appl. No.: 749,618

[22] Filed: Jun. 26, 1985

[51] Int. Cl.[4] .............................................. C07C 121/75
[52] U.S. Cl. ..................................... 558/351; 549/58; 549/75; 549/426; 549/491
[58] Field of Search ................ 260/465 F; 549/58, 75, 549/426, 491; 558/351

[56] References Cited

FOREIGN PATENT DOCUMENTS

| 109681 | 5/1984 | European Pat. Off. . |
| 132392 | 1/1985 | European Pat. Off. . |
| 135691 | 4/1985 | European Pat. Off. . |
| 58-29757 | 2/1983 | Japan . |

OTHER PUBLICATIONS

Oku, J. et al., *J.C.S. Chem. Comm.*, pp. 229–230 (1981).
Oku, J. et al., *Makromol. Chem.*, 183, pp. 579–586 (1982).
Oku, J., *Kagaku Kogyo*, 32 (11), pp. 1134–1136 (62–64), Nov. 1981 and translation.

*Primary Examiner*—Dolph H. Torrence

[57] ABSTRACT

Chiral aromatic cyanohydrins are prepared by treating an aromatic aldehyde with cyanide ions in the presence of an inert, aprotic solvent and a chiral cyclo(phenylalanyl-histidine) and an alcohol. The technique is especially useful for reducing the induction period when starting-up the process, increase the rate of reaction and to produce a product of increased enantiomeric selectivity.

21 Claims, No Drawings

CHIRAL CYANOHYDRINATION PROCESS

BACKGROUND OF THE INVENTION

1. Field of the Invention

The present invention relates to a method of preparing chiral aromatic cyanohydrins.

2. Description of the Prior Art

Chiral aromatic cyanohydrins, including optically-active alpha-hydroxy benzonitriles are known in the art and are of interest, per se, and as intermediates, e.g. to esters. In pyrethroid esters, those having an alpha-S-alpha-hydroxynitrile moiety coupled with the appropriate pyrethroid acid usually have the highest pesticidal activity. However, such alpha-S-alpha-hydroxynitriles have not been particularly easy to obtain in the past because they were usually prepared by resolution.

Asymmetric synthesis of R-mandelonitrile by addition of hydrogen cyanide to benzaldehyde in the presence of a synthetic dipeptide catalyst is known in the art, as in Oku, Jun-ichi and Shohei Inoue, *J.C.S. Chem. Comm.*, pages 229–230 (1981), and other Oku publications where, e.g., cyclo(L-phenylalanyl-L-histidine) containing ½ mole of water of crystallization was used. However, it has been found that the process with cyclo(L-phenylalanyl-L-histidine) and cyclo(D-phenylalanyl-D-histidine) are not necessarily satisfactory or optimal for the preparation of chiral cyanohydrins because of problems with the extent of the induction time for the process and the associated problem of controlling heat released by addition of cyanide ions. Applicants have now found that these problems can be avoided while also increasing further the enantiomeric selectivity of the chiral cyanohydrin product.

SUMMARY OF THE INVENTION

The present invention is directed to a process of preparing a chiral aromatic cyanohydrin (optically-active alpha-hydroxynitrile) or a mixture enantiomerically enriched therein which comprises treating an aromatic aldehyde with cyanide ions in the presence of an inert, aprotic solvent, a cyclo(D-phenylalanyl-D-histidine) or cyclo(L-phenylalanyl-L-histidine) dipeptide as a catalyst and an alcohol.

The presence of an alcohol at the startup of the process has several positive effects including reducing the induction period, increasing the rate for conversion of the aldehyde to chiral cyanohydrin, increasing the enantiomeric selectivity of the chiral cyanohydrin product and controlling heat release associated with the addition of cyanide ions. While not limiting the invention in any way, the positive effects on chiral cyanohydrination produced by the presence of an alcohol are believed to be associated with the acceleration of swelling of the dipeptide catalyst when an alcohol is present.

Any alcohol that will not interfere with the reaction and in which the catalyst is at least slightly soluble can be used in the process, including alcohols R-OH in which the hydrocarbyl group R is alkyl or aralkyl containing up to about 14 carbon atoms optionally substituted by one or more halogen atoms having an atomic number of from 9 to 35 or by alkyl or alkoxy groups in which the alkyl portion contains from 1 to 4 carbon atoms. For example, the alcohol can be alkanol of 1 to 10 carbon atoms, such as, methanol, ethanol, propanol and the like, an aralkyl alcohol containing from 7 to 14 carbon atoms, such as benzyl alcohol, phenylethanol, and the like.

In one embodiment, the alcohol is itself a cyanohydrin and therefore is conveniently the same (chiral) cyanohydrin as the desired product, which in fact, usually is a recycle of a portion of the product chiral cyanohydrin used in the startup of a subsequent process or subsequent batch.

Thus the present invention is directed to a process for the preparation of chiral aromatic cyanohydrins (optically-active alpha-hydroxynitriles) or a mixture enantiomerically enriched therein which comprises treating the corresponding aldehyde with a source of hydrogen cyanide in a substantially water-immiscible, aprotic solvent and in the presence of a cyclo(D-phenylalanyl-D-histidine) or (L-phenylalanyl-L-histidine) dipeptide as a catalyst and in the presence of an alcohol. These products of formula I are then optically-active, optionally-substituted alpha-cyano alcohols or a mixture enantiomerically enriched in such an alcohol.

The chiral aromatic cyanohydrin products include those of formula I

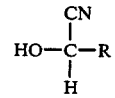

wherein R is an optionally-substituted carbocyclic or an O- or S-heterocyclic aromatic group containing up to 20 carbon atoms. Examples of carbocyclic aryl groups include phenyl, 1-naphthyl, 2-naphthyl and 2-anthryl groups. O- or S-heterocyclic aromatic groups include those derived from hetero-aromatic compounds defined as in Kirk-Othmer, "Encyclopedia of Chemical Technology", Second Edition, Volume 2 (1963), page 702: obtained by replacement of one or more carbon atoms of a carbocyclic aromatic compound by an O- or S-heteroatom including those heterocyclic compounds having five-membered rings which show aromatic characteristics for example, pyran, thiophene, furan, benzothiophene and the like. Optional substitutents include one of more of halogen atoms having an atomic number of from 9 to 35, inclusive; or an alkyl, alkenyl or alkoxy group containing 1 to 6 carbon atoms, each optionally substituted by one or more halogen atoms; optionally substituted phenoxy, phenyl, benzyl or benzoly and equivalent kinds of substituents.

In one embodiment, the alpha-hydroxynitrile has the formula II

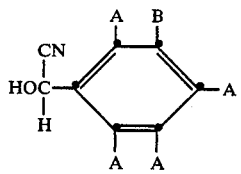

wherein each A is independently a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; B is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; or is a group

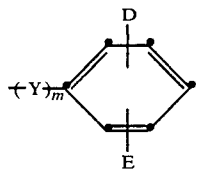

in which Y is O, CH₂, C(O); m is 0 or 1 and D and E each independently is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive.

Preferably, the optically-active alpha-hydroxynitrile products have the alpha-S-configuration when derived from aldehydes and, therefore, include alpha-S alpha-hydroxynitriles of the formula III

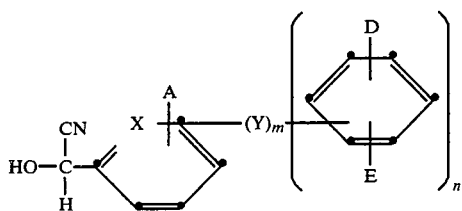

wherein n is 1; m is 0 or 1; Y is O, CH₂, C(O); A, D and E each independently is a hydrogen atom, a halogen atom having an atomic number of from 9 to 35, inclusive, or an alkyl or alkoxy group containing 1 to 6 carbon atoms, each optionally substituted by one or more halogen atoms having an atomic number of from 9 to 35, inclusive. Preferably, Y is O. Preferably, A, D or E each independently is a hydrogen atom, a fluorine atom, a chlorine atom, a methyl group, a trifluoromethyl group or a methoxy group. Preferably, one of D and E each is a hydrogen atom. An especially preferred embodiment of the alpha-S alpha-hydroxynitriles are those of the formula above in which D is a hydrogen atom and A and E each independently is a fluorine atom or a hydrogen atom, and preferably, when either A or E is fluorine, each is located at the 4-position of the ring relative to the benzyl carbon when A or relative to the Y=O bearing carbon atom when E. Especially suitable alcohols are when A is a fluorine atom at the 4position and E is a hydrogen atom.

Non-limiting examples of alpha-hydroxynitriles of the formula I include
S-alpha-cyano-3-phenoxybenzyl alcohol,
S-alpha-cyano-4-fluoro-3-phenoxybenzyl alcohol,
S-alpha-cyano-3-(4-fluorophenoxy)benzyl alcohol, and the like.

In another embodiment of the process, the chiral cyanohydrin has the formula IV

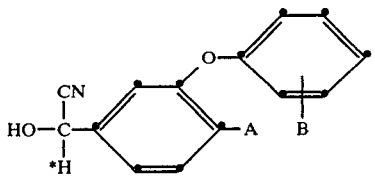

wherein * denotes an asymmetric carbon atom: and A and B each independently is a hydrogen atom, a halogen atom having an atomic number of from 9 to 35, inclusive, or an alkyl or alkoxy group containing 1 to 6 carbon atoms, each optionally substituted by one or more halogen atoms having an atomic number of from 9 to 35, inclusive.

Another embodiment of the invention is directed to a process for starting up a process of chiral cyanohydrination in which an aromatic aldehyde is treated with cyanide ions in the presence of an inert, aprotic solvent and a chiral cyclo(phenylalanyl-histidine) catalyst that which comprises adding to the process an alcohol in an amount sufficient to reduce the induction period of the process.

A further embodiment of the invention is directed to a process for increasing the conversion rate and enantiomeric selectivity in chiral cyanohydrination of an aromatic aldehyde with cyanide ions in the presence of an inert, aprotic solvent and a chiral cyclo(phenylalanyl-histidine) catalyst that comprises adding an alcohol in an amount sufficient to increase the rate of conversion of the aldehyde.

A substantially water-immiscible, aprotic solvent for use in this invention is defined as an aprotic solvent in which the solubility in water is not more than 5%v at the reaction temperature (and does not interfere with the reaction). For example, the solvent is a hydrocarbon or ether solvent including acyclic, alicyclic or aromatic materials. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Useful ethers include diethyl ether, diisopropyl ether, methyl t-butyl ether and the like. Preferably, the solvent has a boiling point below about 150° C. Preferably, the solvent is an aromatic hydrocarbon, especially toluene, diisopropyl ether or diethyl ether or mixtures thereof (e.g. 25/75 of diethyl ether/toluene). Toluene gives especially high enantiomeric excess when the substrate is 3-phenoxybenzaldehyde. Advantages of diethyl ether are that the rate of reaction is increased and the catalyst is not soluble and can be recovered as a solid at the end of the reaction.

The amount of catalyst can vary. For example, it can be used in the range of from about 0.1 to about 10 mole percent based upon the weight of the aldehyde present, especially about 1.0 to about 7.5 mole percent. The catalyst is preferably well dispersed in the reaction mixture.

The reaction is started-up or conducted in the presence of an alcohol in sufficient amount to accomplish the desired result of reducing the induction period, increasing the rate of conversion, increasing the enantiomeric selectivity and/or controlling the heat release associated with the addition of cyanide ions and can readily be determined by one skilled in the art but is usually between about 0.1 to about 25% weight based on the weight of the equivalent product chiral cyanohydrin to be produced. The amount may also vary somewhat by which alcohol that is used. When the alcohol is the same (chiral) cyanohydrin as the desired product, the amount used is from about 3% to about 15% weight based upon the weight of the equivalent product chiral cyanohydrin to be produced. In the case of lower alkanols, e.g. methanol, as little as 0.1% weight will reduce the induction period.

The aromatic aldehyde reactant corresponds to the desired chiral cyanohydrin product, e.g., of formulas I, II, III or IV, and preferably, is an aldehyde reactant of the formula V

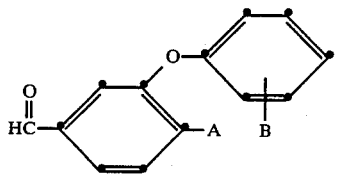

V wherein A and B have the same meanings as given in the formula IV above.

Examples of suitable aldehydes of the formula above include 3-phenoxybenzaldehyde, 4-fluoro-3-phenoxybenzaldehyde, and the like.

The source of cyanide ions is hydrogen cyanide or an agent that generates hydrogen cyanide, under the reaction conditions. Hydrogen cyanide itself is preferred. The molar ratio of hydrogen cyanide to aldehyde is from about 1.0 to about 3.0 moles per mole of aldehyde and, preferably, from about 1.1 to about 2.0.

The preferred embodiment of the present invention is directed to use a catalyst for cyanohydrination of aldehydes, comprising a solid chiral cyclo(phenylalanyl-histidine) having a substantially non-crystalline component as claimed in co-pending U.S. Ser. No. 535,500, filed Sept. 26, 1983, and subsequent divisions thereof, and U.S. Ser. No. 551,548, filed Nov. 14, 1983 as a continuation-in-part of U.S. Ser. No. 443,763, filed Nov. 22, 1982 (now abandoned) and also described below.

In other words, the catalyst has a component having a substantially amorphous or non-crystalline structure. While the precise form of this cyclo(D-phenylalanyl-D-histidine) or cyclo(L-phenylalanyl-L-histidine) dipeptide is not known, it appears that the activated (amorphous or non-crystalline) form precipitated with a random structure and with a number of the available —NH groups in the dipeptide free of intermolecular hydrogen bonding to the available —C=O groups as compared with the less active (crystalline component) form where the molecules had time to orient themselves as they were laid down into a highly-bonded orderly structure. Such being the case, the degree of amorphousness or non-crystallinity is most readily determined by X-ray diffraction.

The wide-angle X-ray scattering (WAXS) measurements were carried out in reflection by means of a Philips APD3600/02 automated X-ray diffractometer. The samples were scanned at 20° C. in air from 5.0° to 60.0° $2\theta$ at 0.02 degree increments, and 0.6 second time increments with Cu K$\alpha$ radiation (40KV, 35ma).

The percent crystallinity was determined by a modified Hermans and Weidinger method (P. H. Hermans and A. Weidinger, *Makromol. Chem.*, 50, 98 (1961)). The diffuse background scattering below the main peaks was constructed with a consistent baseline between $5° \leq 2\theta \leq 60°$ and approximating the amorphous scattering with a smooth curve. The X-ray crystallinity, $W_c$, was calculated from the integrated crystalline and amorphous intensities $F_c$ and $F_a$ by the equation $W_c = F_c/(F_c + F_a)$. The various definitions can be found in the text H. P. Klug and L. E. Alexander, *X-Ray Diffraction Procedures for Polycrystalline and Amorphous Materials*, Wiley-Interscience, New York, (1974).

As used herein the terms "amorphous" or "non-crystalline" define active catalyst materials that have about 45% or more of an amorphous or non-crystalline component as determined by the area of the X-ray diffraction spectra obtained by the method described above. Preferably, the "amorphous" or "non-crystalline" component of the materials as defined by the X-ray diffraction spectra is about 45% to about 65% or higher. Preferably, the "amorphous" or "non-crystalline" component is about 65% or higher.

The catalysts are also analyzable by photomicrographs in which inefficient catalysts consist of agglomerates of fine crystallites. Crystallites are not evident in photomicrographs of active catalysts, which when, for example, are spray-dried, take the form of hollow-appearing spheres. Alternative methods are available to define the terms amorphous and non-crystalline character as by infrared or nuclear magnetic resonance spectral studies or by swelling of the material, e.g. in contact with the reactants of the cyanohydrination process.

In a preferred method the dipeptide is prepared by the route described below in which HIS means histidine and PHE means phenylalanine.

Histidine O—Methylation

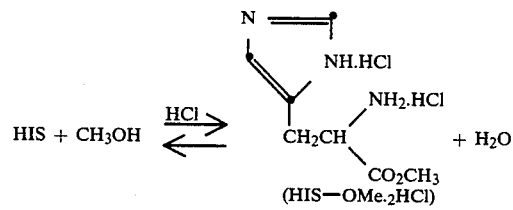

Leuchs' Anhydride Formation

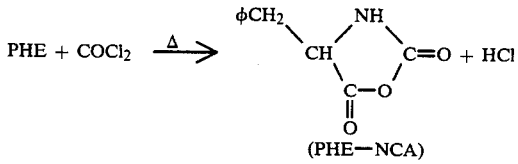

Coupling

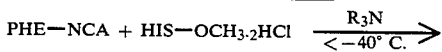

-continued

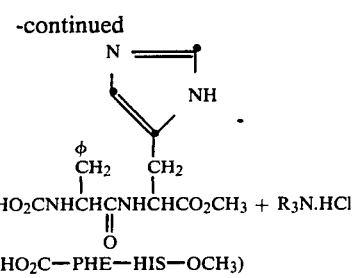

(HO₂C—PHE—HIS—OCH₃)

Carbamic Acid Decomposition

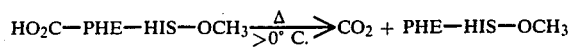

Cyclization

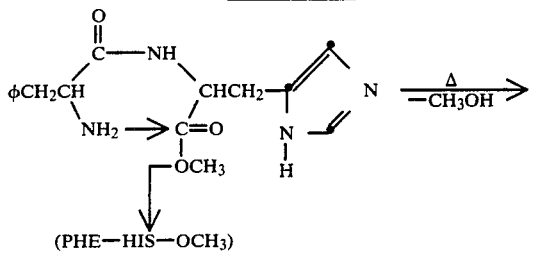

(PHE—HIS—OCH₃)

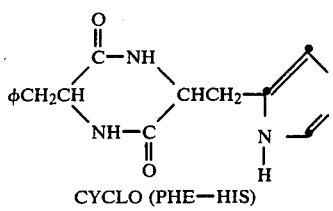

CYCLO (PHE—HIS)

When the catalyst is prepared by conventional methods in the presence of water, and as a solid, it can also contain solvent (e.g. water) of crystallization and thus includes the presence of absence of solvent (e.g. water) of crystallization.

The solid catalyst can be recovered by extraction with acid followed by neutralization of the extract with a base or preferably by treating with or (dissolving in) a solvent, for example a hydroxylic solvent, including lower alkanols of 1 to 10 carbon atoms such as isopropanol or preferably methanol (preferably with heating, e.g. to reflux or quick flash), and repreciprocating (preferably below ambient temperature) to produce a less crystalline (more amorphous) catalyst structure.

While it is preferred to directly prepare the catalyst of the present invention having the non-crystalline component, it is also within the scope of this invention to prepare a substantially crystalline catalyst and subsequently to activate the catalyst by converting at least part of the crystalline material to an amorphous form. Thus, the present invention is directed to both a method of directly preparing an active cyclo(D-phenylalanyl-D-histidine) or cyclo(L-phenylalanyl-L-histidine) dipeptide catalyst and to a method of activating a crystalline catalyst of this type, which methods both involve reducing or preventing the formation of a substantially crystalline form thereof. In the case of activation of a crystalline catalyst, the crystalline form is first broken down and then prevented at least in part from reforming. It is believed that the breakdown of or the prevention of the formation of a number of intermolecular bonds between the amino N—H and the carboxyl C=O groups in the crystal lattice makes the catalyst have an amorphous or non-crystalline form. In any event, an ordered deposition of crystals of the catalyst is discouraged or reduced.

Any means which will accomplish this reduction or prevention either during the catalyst preparation or an after treatment are within the scope of the invention. Among the illustrative examples of methods which reduce or prevent the formation of a highly crystalline form or highly ordered arrangement are (a) very rapid evaporation of a solution of the catalyst, in the presence or absence of impurities or crystallinity inhibitors; (b) rapid precipitation of the catalyst from solution by dilution in a poor solvent; (c) freeze drying of a solution of the catalyst; (d) rapid cooling of the melted catalyst in the presence or absence of impurities or crystallinity inhibitors; (e) use of crystallinity inhibitors during solidification; and the like.

The unactivated dipeptide catalyst, when recovered at the end of a conventional synthesis process, is often almost completely inactive in the cyanohydrination reaction, apparently because it has become highly crystalline as can be determined by X-ray diffraction. Activation, as used herein, appears to involve converting at least part of the normally crystalline material into an amorphous form such that the dipeptide is swelled by the reaction mixture and the chiral base function of the catalyst is made accessible to the reactants. In order to produce high chirality in the cyanohydrination product, it appears that the catalyst should preferably be essentially insoluble in the cyanohydrination solvent.

The first step in converting what is or what normally would be a crystalline material to an amorphous form is to break down (or prevent) formation of the intermolecular bonds in the crystal lattice. The breakdown readily occurs when the material is melted or dissolved in a solvent. Once this has been accomplished, a method is used that will allow the separation of the dissolved material from the solvent at a rate such that normal crystallization cannot occur. There are a number of ways in which this might be effected: (a) rapid evaporation of the solvent, e.g. as in a spray dryer; (b) rapid precipitation of the material by pouring a solution of it into a large volume of a different solvent that is miscible with the original solvent but does not dissolve, to a large extent, the material to be precipitated; (c) rapid freezing of a solution followed by sublimation of the solvent (freeze drying); (d) rapid cooling of the melted catalyst; and (e) use of inhibitors alone or with any of the above methods (a)–(d). Preferably, the method used is (a) rapid evaporation of the solvent and, especially, by means of spray drying.

Because of the polar nature and high melting point (~250° C.) of the chiral cyclo(phenylalanyl-histidine), the choice of solvents that will dissolve it to any appreciable extent is very limited. Potential solvents suitable and unsuitable that have been tested are listed in Table 1 in order of decreasing effectiveness, and the use of these will be discussed below in relation to the method of catalyst activation via recovery techniques or specific subsequent activation treatment.

TABLE 1

| SOLVENTS TESTED FOR SOLUBILITY OF CYCLO(D-PHENYLALANYL-D-HISTIDINE) | | |
|---|---|---|
| Solvent | B.P./°C. | Solvency |
| Dimethyl Sulfoxide | 189 | Good (5–10% w) |
| Acetic Acid | 118 | Good |
| Formamide | 210 | ≧2.3% at 25° C. |

TABLE 1-continued

SOLVENTS TESTED FOR SOLUBILITY OF
CYCLO(D-PHENYLALANYL-D-HISTIDINE)

| Solvent | B.P./°C. | Solvency |
| --- | --- | --- |
| 1-Methyl-2-pyrrolidinone | 202 | ≧2.2% at 25° C. |
| Dimethylformamide | 153 | Fair to Good, <5% at 90° C. |
| Liquid Ammonia | −33 | ~2% at −40° C. |
| N—methylformamide | 185 | ≧2.4% at 25° C. |
| Acetonitrile | 80 | Fair to Poor, <<5% at 70° C. |
| Methanol | 64 | 1% w Hot, 0.3% w at 25° C. |
| Water | 100 | 1% at 75° C., 0.2% at 25° C. |
| Acetone | 55 | Fair to Poor, <<1% at 25° C. |
| Liquid Carbon Dioxide | −78 | Poor, <0.2% at 25° C. |
| Carbon Disulfide | 45 | Very Poor |
| Diethyl Ether | 35 | Very Poor |
| Hydrocarbons | Var. | Very Poor |

The use of crystallization inhibitors is an alternative method of reducing or preventing the crystalline form of the dipeptide. Many chemicals can be used. It is useful if the crystallization inhibitor has a similar kind of structure or has one or more substituents similar in kind to those found in the dipeptide, but the inhibitor is not identical to the units of the dipeptide. In the case of this dipeptide, useful kinds of crystallization inhibitors include those materials containing a —N—H and/or —C=O group, including ureas and aldehydes. Even by-product impurities of the dipeptide process containing such substituents are useful crystallization inhibitors, e.g. making an impure product can make a more active catalyst.

The reaction to prepare alpha-hydroxynitriles is suitably conducted by adding the aldehyde and solvent to the chiral cyclo(phenylalanyl-histidine) dipeptide catalyst, dispersing (mechanical grinding or agitating the mixture, e.g. by stirring) adding hydrogen cyanide and maintaining the reaction conditions for an amount of time to effect the formation of the optically-active alpha-hydroxynitrile. That is, preferably, the hydrogen cyanide is introduced concurrently with or subsequent to the solvent and/or aldehyde to increase the conversion and stereoselectivity. The presence of cyanide ions appears to have an adverse effect on the catalyst in this reaction. The forming and maintaining of a well dispersed but not necessarily homogenous-like reaction mixture are useful. Separation and recovery of the optically-active ester product are achieved by conventional techniques, including extraction and the like.

The temperature of the reaction to prepare the chiral alpha-hydroxynitriles as well as the pressure can vary. At normal pressures, the temperature is from about −10° C. to about 80° C., more or less. Preferably, ambient temperatures of about 5° C. to about 35° C. are convenient to give blood yield, rate of reaction and enantiomeric excess of the desired optically-active product, the lower temperature of about 5° C. giving good results.

The alpha-hydroxynitriles and their corresponding aldehydes are generally known in the literature. The S-benzyl alcohols are of interest per se or as intermediates to esters, e.g. of the pyrethroid type, for example, S-alpha-cyano-3-phenoxybenzyl alcohol in U.S. Pat. No. 4,273,727.

The S-alpha-cyano-3-phenoxybenzyl alcohol or mixture enriched therein of the invention, is treated with a carboxylic acid halide, e.g., an S-alpha-isopropylphenylacetic acid chloride or an optionally-substituted chiral cyclopropanecarboxylic acid chloride, to give an optically-active cyanomethyl ester or a mixture enriched therein. The cyanomethyl esters for which the optically-active form is prepared from one or more chiral cyanohydrins of the process of the invention, have e.g. the formula VI $$R-\overset{O}{\underset{\parallel}{C}}-O-\overset{CN}{\underset{*H}{C}}- \text{[Ar-O-Ar]} -A \quad B \qquad VI$$

in which $$\overset{O}{\underset{\parallel}{RCO}}-$$

is the residue of a carboxylic acid of the pyrethroid type, which are generally known in the art, including in the optical forms, from e.g., U.S. Pat. Nos. 4,151,195, 4,239,737, 4,328,167 and 4,133,826, and British Pat. No. 2,014,137 and the like. Preferably, the product optically-active ester is S-alpha-cyano-3-phenoxybenzyl S-alpha-isopropyl(p-chlorophenyl)acetate, S-alpha-cyano-3-phenoxybenzyl S-alpha-isopropyl(p-(difluoromethoxy)phenyl)acetate, S-alpha-cyano-3-phenoxybenzyl (1R,cis)-3-(2,2-dichlorovinyl)-2,2-dimethylcyclopropanecarboxylate, S-alpha-cyano-3-phenoxybenzyl (1R,cis)-3-(2,2-dibromovinyl)-2,2-dimethylcyclopropanecarboxylate, S-alpha-cyano-3-phenoxybenzyl (1R,cis)-3-(1,2-dibromo-2,2-dichloroethyl)-2,2-dimethylcyclopropanecarboxylate, S-alpha-cyano-3-phenoxybenzyl (1R,cis)-2,2-dimethyl-3-(neopentoxyiminomethyl)cyclopropanecarboxylate, and the like.

ILLUSTRATIVE EMBODIMENTS

The following embodiments are provided for the purpose of illustrating the invention and should not be regarded as limiting it in any way. The identity of the products was confirmed by infrared and nuclear magnetic resonance spectral analyses.

EMBODIMENT 1

A Nitro Atomizer laboratory spray dryer with a ca 31 inch diameter chamber was assembled. In operation, 40 SCFM $N_2$ is heated to 140° C. and fed to the dryer chamber. A warm solution of 0.5–1.0%w cyclo(D-phenylalanyl-D-histidine) in methanol is fed via a rotary vaned atomizer to the chamber above the $N_2$ inlet. The droplets of cyclo(D-phenylalanyl-D-histidine) solution are rapidly dried to give hollow spherical particals of 1 to 10 μm diameter. The combined stream is fed to a cyclone where 50–70% of the particles are captured.

Seven test runs were made using 5 to 10 gm of cyclo(D-phenylalanyl-D-histidine) each. Starting with a catalyst that was inefficient for cyanohydrination, all the products were activated to give good reaction rate and produce (S)-alpha-cyano-3-phenoxybenzal alcohol with EE's between 75–80% at 97% conversion of 3-phenoxybenzaldehyde. Water and sodium chloride, simulating recycle operation, apparently had no effect on activation. On the other hand, the addition of urea to further disrupt crystallization of cyclo(D-phenylalanyl- D-histidine) did not result in any further improvement. The results of the seven test runs are tabulated in Table 2.

ment, on the other (Experiment 4). In both cases the products had about the same activity (conversion/selectivity: 93%/72%.

TABLE 2

ACTIVATION OF CYCLO(D-PHENYLALANYL-D-HISTIDINE) BY SPRAY DRYING

| Experiment | Catalyst Purity % w | Feed Composition (Rest MeOH) | | | | Feed Rate ml/min | $N_2$ Rate $SCFM^f$ | Temp In °C. |
|---|---|---|---|---|---|---|---|---|
| | | $DDCAT^d$ % w | $H_2O$ % w | NaCl % w | Others % w | | | |
| 1 | 87 | 0.49 | | | | 115 | 42 | 135 |
| 2 | 87 | 0.48 | | | | 225 | 42 | ~160 |
| 3 | $92^b$ | 0.84 | | | | 125 | 43 | 135–140 |
| 4 | $92^b$ | 0.63 | 4.5 | | | 110 | 43 | 139 |
| 5 | $92^b$ | 0.62 | 4.5 | 1.0 | | 135 | 43 | 137–140 |
| 6 | $92^b$ | 0.65 | — | — | 0.033 | 125 | 43 | 139 |
| 7 | $92^b$ | 0.80 | — | — | — | 135 | 42 | 135–140 |

| Experiment | Temp Out °C. | Atomizer RPM × $10^{-3}$ | Catalyst Recovery % | Particle Size μm | Cyanohydrination In Toluene at 25° C. | | |
|---|---|---|---|---|---|---|---|
| | | | | | Time hr | $POAL^e$ Conversion % | (S)—$POAL.CN^e$ Selectivity % |
| 1 | 60–75 | 37 | 46 | 1–12 | 1 | 92.2 | 91 |
| | | | | | 2 | 95.9 | 90 |
| | | | | | 4 | 96.9 | 90 |
| | | | | | 5.5 | 95.9 | 90 |
| 2 | 60–70 | 31 | 58 | 1–12 | 1 | 91.3 | 90 |
| | | | | | 3 | 95.5 | 88 |
| | | | | | 4 | 96.7 | 88 |
| | | | | | 5.1 | 98.4 | |
| 3 | 55–65 | 37 | $66^a$ | 1–10 | 1 | 93 | 90 |
| | | | | | 2 | 96.7 | 90 |
| | | | | | 3 | 96.6 | 92 |
| | | | | | 4 | 97.6 | 90 |
| 4 | 65–75 | 36 | $56^a$ | 1–10 | 1 | 94.6 | |
| | | | | | 2 | 96.9 | 90 |
| | | | | | 3 | 98.7 | 89 |
| 5 | 55–65 | 36 | 68 | 1–10 | 1 | 93.6 | 91 |
| | | | | | 2 | 96.6 | 90 |
| | | | | | 3 | 95.4 | 91 |
| | | | | | 4 | 97.5 | 90 |
| | | | | | 5 | | 90 |
| 6 | 70–75 | 36 | 58 | 1–10 | 1 | 92.3 | 90 |
| | | | | | 2 | 91.0 | 90 |
| | | | | | 4 | 94.7 | 89 |
| | | | | | 5 | 96.0 | 90 |
| 7 | 55–70 | 38 | 77 | 1–10 | 1 | 93.3 | 93 |
| | | | | | 2 | 96.1 | 91 |
| | | | | | 3 | 95.9 | 92 |
| | | | | | 4 | 97.6 | 92 |
| | | | | | 5 | 96.0 | 91 |

$^a$Mostly held in cyclone by static electricity.
$^b$96% purity by potentiometric titration.
$^c$EE = 2 (selectivity) - 100, %.
$^d$DDCAT = cyclo(D-phenylalanyl-D-histidine)
$^e$POAL = 3-phenoxybenzaldehyde, (S)—POAL.CN = (S)—α-cyano-3-phenoxybenzyl alcohol.
$^f$SCFM = standard cubic feet per minute.

EMBODIMENT 2

Another method tested for activating the catalyst is freeze drying. This approach requires a solvent for the dipeptide that freezes at a convenient temperature and is volatile enough to be sublimed at below that temperature and at a practical pressure (vacuum). Of the solvents tested, only water and acetic acid meet these requirements. The results of some of these tests are summarized in Table 3. Freeze drying of a 0.1%w solution of the dipeptide in water gave an excellent product (Experiment 5). An attempt to freeze dry a solution in dimethyl sulfoxide failed because the solvent was too high boiling to be sublimed at about 0° C. and 170 microns pressure. On the other hand, solutions in glacial acetic acid were readily freeze dried. The product from this freeze drying contains one mole of acetic acid per mole of catalyst. In spite of this, the product was surprisingly active and selective (Experiment 2). This acid is relatively loosely held by the catalyst, and it was volatilized away in a sweep of air, on the one hand (Experiment 3), or neutralized by triethylamine treat-

TABLE 3

ACTIVATION OF CYCLO(D-PHENYLALANYL-D-HISTIDINE) BY FREEZE DRYING

| Experiment | Solvent/Work Up | Cyanohydrination$^{(b)}$ | |
|---|---|---|---|
| | | Conversion %/3 Hr | Enantiomeric Excess, %$^{(a)}$ |
| 1 | From 2% solution in dimethyl sulfoxide | — | — |
| 2 | From 1.9% solution in acetic acid | 74 | 56 (6.5) |
| 3 | Product from experiment 2 air swept 2 days | 93 | 73 (5) |
| 4 | Product from Experiment 2 treated with triethylamine in diethyl ether | 93 | 72 (6.3) |
| 5 | From 0.1% solution in water | 98 | 85 (2.5) |

$^{(a)}$Numbers in parentheses indicate time, in hours.
$^{(b)}$Cyanohydrination of 3-phenoxybenzaldehyde with HCN to give (S)—alpha-cyano-3-phenoxybenzyl alcohol.

EMBODIMENT 3

Cyclo(D-phenylalanyl-D-histidine) catalyst was dispersed in a solution of 3-phenoxybenzaldehyde (POAL) in toluene and the resulting mixture was treated with 1.25 m/Kg of hydrogen cyanide at 5° C. under nitrogen. In experiment 2-4, a specified amount of S-alpha-cyano-3-phenoxybenzyl alcohol, Z, (e.g., amount recycled from a previous batch) was added to the reaction mixture. Results of these experiments are set forth in Table 4 below.

TABLE 4
EFFECT OF ALCOHOL Z ON CYANOHYDRINATION

| Embodiment | % Alcohol-Z Added | % S—alcohol-Z Isomer Produced at 6.5 Hr. | % POAL Conversion 1 Hr. | % POAL Conversion 6.5 Hr. |
| --- | --- | --- | --- | --- |
| 1 | 0 | 91 | 20 | 94 |
| 2 | 3.5 | 94.9 | 74 | 95 |
| 3 | 6.6 | 95.2 | 82 | 95 |
| 4 | 13.0 | 95.6 | 87 | 96 |

EMBODIMENT 4

Cyclo(D-phenylanyl-D-histidine) catalyst was dispersed in a solution of 1 m/Kg of 3-phenoxybenzaldehyde (POAL) in toluene and the resulting mixture was treated with 1.25-1.3 m/Kg of hydrogen cyanide at 5° C. under nitrogen. In experiments 1-3, a specified amount of an alkanol was added to the reaction mixture. Results of these experiments are set forth in Table 5 below.

TABLE 5
EFFECT OF ALCOHOLS ON CYANOHYDRINATION

| Embodiment | Alcohol Additive | Conc.(a) % w. | Time Hr. | POAL Conv. % | % S—alcohol Isomer |
| --- | --- | --- | --- | --- | --- |
| 1 | MeOH | 0.6 | 1 | 67 | |
| | | | 3 | 91 | |
| | | | 6.5 | 96.5 | 93.9 |
| 2 | MeOH | 0.6 | 1 | 75 | |
| | | | 3.5 | 92 | |
| | | | 6.5 | 97 | 93.4 |
| 3 | MeOH | 0.2 | 1 | 63 | |
| | | | 3.5 | 88 | |
| | | | 6.5 | 95 | 93.5 |
| 4 | None | — | 1 | 30 | |
| | | | 3.5 | 86 | |
| | | | 6.5 | 95 | 92.3 |

(a)Basis total reactor charge.

What is claimed is:

1. A process for the preparation of a chiral cyanohydrin or a mixture enantiomerically enriched therein which comprises treating an aromatic aldehyde in an inert, aprotic solvent with cyanide ions in the presence of a cyclo(D-phenylalanyl-D-histidine) or cyclo(L-phenylalanyl-L-histidine) dipeptide catalyst and an aralkyl alcohol.

2. A process according to claim 1 wherein the solvent is an aromatic hydrocarbon, an ether or mixtures thereof.

3. A process according to claim 2 wherein the solvent is toluene.

4. A process according to claim 2 wherein the alcohol has the formula R—OH in which R is aralkyl containing up to about 14 carbon atoms optionally substituted by one or more halogen atoms having an atomic number of from 9 to 35 or by alkyl or alkoxy groups in which the alkyl portion contains from 1 to 4 carbon atoms.

5. A process according to claim 3 wherein the aralkyl alcohol is the same chiral cyanohydrin as the desired product and is recycled from a previous batch or process.

6. A process according to claim 3 wherein the chiral cyanohydrin product is cyanohydrin of formula IV

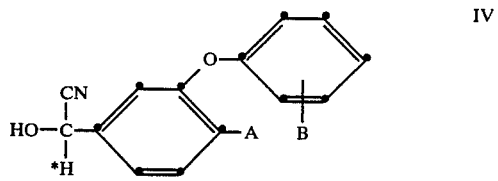

wherein * denotes an asymmetric carbon atom and A and B each independently is a hydrogen atom, a halogen atom having an atomic number of from 9 to 35 inclusive, or an alkyl or alkoxy group containing 1 to 6 carbon atoms, each optionally substituted by one or more halogen atoms having an atomic number of from 9 to 35, inclusive, or a mixture enriched therein.

7. A process according to claim 6 wherein the chiral cyanohydrin product and the aralkyl alcohol each is S-alpha-cyano-3-phenoxybenzyl alcohol.

8. A process for starting up a process of chiral cyanohydrination in which an aromatic aldehyde is treated with cyanide ions in the presence of an inert, aprotic solvent and a chiral cyclo(phenylalanyl-histidine) which comprises adding to the process an aralkyl alcohol in an amount sufficient to reduce the induction period of the process.

9. A process according to claim 8 wherein the solvent is an aromatic hydrocarbon, an ether or mixtures thereof.

10. A process according to claim 9 wherein the solvent is toluene.

11. A process according to claim 9 wherein the alcohol has the formula R—OH in which R is aralkyl containing up to about 14 carbon atoms optionally substituted by one or more halogen atoms having an atomic number of from 9 to 35 or by alkyl or alkoxy groups in which the alkyl portion contains from 1 to 4 carbon atoms.

12. A process according to claim 10 wherein the aralkyl alcohol is the same chiral cyanohydrin as the desired product and is recycled from a previous batch or process.

13. A process according to claim 10 wherein the chiral cyanohydrin product is cyanohydrin of formula IV

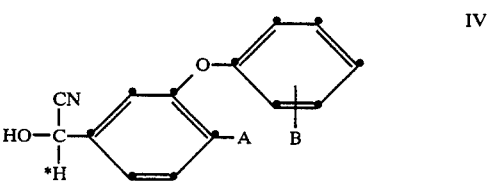

wherein * denotes an asymmetric carbon atom; and A and B each independently is a hydrogen atom, a halogen atom having an atomic number of from 9 to 35 inclusive, or an alkyl or alkoxy group containing 1 to 6 carbon atoms, each optionally substituted by one or more halogen atoms having an atomic number of from 9 to 35, inclusive, or a mixture enriched therein.

14. A process according to claim 13 wherein the chiral cyanohydrin product and the aralkyl alcohol each is S-alpha-cyano-3-phenoxybenzyl alcohol.

15. A process for increasing the conversion rate and enantiomeric selectivity in chiral cyanohydrination of an aromatic aldehyde with cyanide ions in the presence of an inert, aprotic solvent and a cyclo(D-phenylalanyl-D-histidine) or cyclo(L-phenylalanylyl-L-histidine) dipeptide catalyst which comprises adding an aralkyl alcohol in an amount sufficient to increase the rate of conversion of the aldehyde.

16. A process according to claim 15 wherein the solvent is an aromatic hydrocarbon, an ether or mixtures thereof.

17. A process according to claim 16 wherein the solvent is toluene.

18. A process according to claim 16 wherein the alcohol has the formula R—OH in which R is aralkyl containing up to about 14 carbon atoms optionally substituted by one or more halogen atoms having an atomic number of from 9 to 35 or by alkyl or alkoxy groups in which the alkyl portion contains from 1 to 4 carbon atoms.

19. A process according to claim 17 wherein the aralkyl alcohol is the same chiral cyanohydrin as the desired product and is recycled from a previous batch or process.

20. A process according to claim 17 wherein the chiral cyanohydrin product is cyanohydrin of formula IV

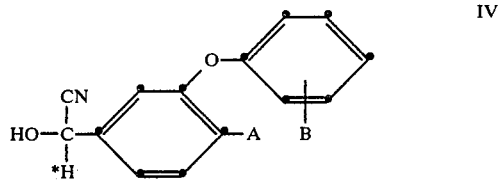

wherein * denotes an asymmetric carbon atom; and A and B each independently is a hydrogen atom, a halogen atom having an atomic number of from 9 to 35 inclusive, or an alkyl or alkoxy group containing 1 to 6 carbon atoms, each optionally substituted by one or more halogen atoms having an atomic number of from 9 to 35, inclusive, or a mixture enriched therein.

21. A process according to claim 20 wherein the chiral cyanohydrin product and the aralkyl alcohol each is S-alpha-cyano-3-phenoxybenzyl alcohol.

* * * * *